United States Patent [19]

Eicken et al.

[11] 4,124,591
[45] Nov. 7, 1978

[54] ISOXAZOLYLMETHYLTHIOL CARBAMATES

[75] Inventors: Karl Eicken, Wachenheim; Hans Theobald, Limburgerhof; Hanspeter Hansen, Ludwigshafen; Bruno Wuerzer; Kurt Fett, both of Limburgerhof, all of Fed. Rep. of Germany

[73] Assignee: BASF Aktiengesellschaft, Ludwigshafen, Fed. Rep. of Germany

[21] Appl. No.: 810,194

[22] Filed: Jun. 27, 1977

[51] Int. Cl.$^2$ .................. C07D 261/08; C07D 413/12

[52] U.S. Cl. .................. 260/307 H; 71/88; 71/94; 71/95; 544/137; 546/209; 546/245

[58] Field of Search .................. 260/307 H, 293.67; 544/137

[56] References Cited

U.S. PATENT DOCUMENTS 3,629,474  12/1971  Ghosh et al. .................. 424/272

Primary Examiner—Raymond V. Rush
Attorney, Agent, or Firm—Keil, Thompson & Shurtleff

[57] ABSTRACT

Isoxazolylmethylthiol carbamates, herbicides containing these compounds, and methods of controlling the growth of unwanted plants with these compounds.

4 Claims, No Drawings

ISOXAZOLYLMETHYLTHIOL CARBAMATES

The present invention relates to new and valuable isoxazolylmethylthiol carbamates, herbicides containing these compounds, and methods of controlling the growth of unwanted plants with these compounds.

It is known from French Pat. No. 2,205,514 that the thiolcarbamic acid esters of imidazole have a herbicidal action.

There is no disclosure of the type of herbicidal activity, e.g., selectivity in and tolerance by crop plants, and application rates. The herbicidal action of the active ingredients is only slight.

Numerous thiol carbmates are known as herbicides. Some of them have achieved considerable importance in agriculture and horticulture for controlling the growth of unwanted plants. A characteristic common to these compounds is the good action on unwanted grasses. However, this action varies from species to species of this family. For instance, N,N-dipropylthiolethyl carbamate controls wild oats (German Published Application DAS 1,031,571), but this species is not listed in the manufacturer's recommendations for N,N-dipropylthiolpropyl carbamate (German Published Application DAS 1,031,571). It is reported that N,N-dipropylthiolethyl carbamate has a good action on Setaria spp., whereas the action of N,N-diisopropylthiol-2,3-dichloroallyl carbamate (German Published Application DAS 1,142,464) was inferior here. In addition to controlling unwanted grasses, some compounds of this class also destroy Cyperaceae and some broadleaved weeds. For instance, N,N-dipropylthiolpropyl carbamate has an extremely reliable action on Cyperus spp., whereas N,N-diisopropylthiol-2,3-dichloroallyl carbamate has practically no effect on these species. An essential criterion for the use of these agents is the difference in selectivity from crop plant to crop plant. Thus, N-ethyl-N-cyclohexylthiolethyl carbamate (British Pat. No. 995,316) is used predominantly in Beta beets. The most important crop plant for N,N-diisobutylthiolethyl carbamate (German Published Application DAS 1,031,571) is Indian corn. This difference is particularly surprising in the case of N,N-diisopropylthiol-2,3-dichloroallyl carbamate and N,N-diisopropylthiol-2,3,3-trichloroallyl carbamate (German Published Application DAS 1,142,464). Both products can be employed without difficulty in broadleaved crops such as beet and rape. For cereals, the manufacturers and distributors only recommend N,N-diisopropylthiol-2,3,3-trichloroallyl carbamate, as it is less aggressive in these crops.

Prior art thiol carbamates have in general a high vapor pressure, as the following list shows:

| Active ingredient | vapor pressure mm Hg | at ° C |
| --- | --- | --- |
| N,N-dipropylthiolethyl carbamate | 34 × 10$^{-3}$ | 25 |
| N,N-diisobutylthiolethyl carbamate | 13 × 10$^{-3}$ | 25 |
| N,N-dipropylthiolpropyl carbamate | 10.4 × 10$^{-3}$ | 25 |
| N-ethyl-N-cyclohexylthiolethyl carbamate | 6.2 × 10$^{-3}$ | 25 |
| N,N-diisopropylthiol-2,3-dichloroallyl carbamate | 1.5 × 10$^{-4}$ | 25 |
| N,N-diisopropylthiol-2,3,3-trichloroallyl carbamate | 1.2 × 10$^{-4}$ | 25 |
| hexahydro-1H-azepin-1-carbamic acid thiolethyl ester (German 1,300,947) | 5.6 × 10$^{-3}$ | 25 |

All these compounds have to be incorporated into the soil to prevent loss through evaporation. In the case of the last compound, the submerging of rice paddies probably has the same effect as incorporation.

Although generally speaking the incorporation of herbicides is positive for a number of reasons, this method of application does have considerable disadvantages, e.g., the work burden is increased, and special incorporation equipment has to be acquired. This makes itself felt particularly at farms having a low degree of mechanization. The seedbed is excessively loosened, and as a consequence certain seeds have emergence difficulties in dry weather. In areas where heavy rainfalls occur, this additional soil treatment increases the risk of erosion, particularly on sloping ground. Similarly, loosening of the soil assists wind erosion in arid wind-swept tracts. For these reasons, attempts are made under the abovementioned conditions to move the soil as little as possible during cultivation ("reduced tillage").

There is therefore a demand for active ingredients which offer an alternative to incorporation. In the field of thiol carbamates with their specific properties, such compounds, with the exception of hexahydro-1H-azepine-1-carbamic acid thiolethyl ester and S-(4-chlorobenzyl)-N,N-diethylthiol carbamate — which are used in rice —, have hitherto not been available. Attempts have recently been made in this direction with the manufacture of thiol carbamate sulfoxides.

We have now found that isoxazolylmethylthiol carbamates of the formula

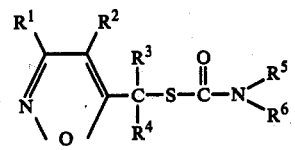

where $R^1$ denotes hydrogen, alkyl, unsubstituted or alkyl-substituted cycloalkyl, aralkyl, or optionally substituted aryl, $R^2$ denotes hydrogen, optionally substituted alkyl, aryl, or halogen, $R^3$ denotes hydrogen or alkyl, $R^4$ denotes hydrogen or alkyl, and $R^5$ and $R^6$ are identical or different and each denotes alkyl, alkenyl, unsubstituted or alkyl-substituted cycloalkyl, alkoxyalkyl or haloalkyl, and additionally $R^5$ and $R^6$ together with the nitrogen atom denote an unsubstituted or lower alkyl-substituted heterocyclic ring having 4, 5, 6 or 7 members, have a strong herbicidal and selective action.

These active ingredients offer, in addition to the wider spectrum of action, a flexibility in the method of application hitherto unknown in this class of compounds.

The radicals R contained in the isoxazolylmethylthiol carbamates of the formula I have for instance the following meanings:

$R^1$ = hydrogen; lower alkyl of a maximum of 6 carbon atoms, e.g., methyl, ethyl, n-propyl, isopropyl, n-butyl, sec-butyl, isobutyl, tert-butyl, n-pentyl, 2-pentyl, 3-pentyl, n-hexyl; cycloalkyl of a maximum of 8 carbon atoms optionally substituted by lower alkyl, e.g., cyclopropyl, cyclopentyl, cyclohexyl, cyclooctyl; aralkyl, e.g., benzyl, 1-phenylethyl, 2-phenylethyl; and optionally substituted aryl, e.g., phenyl, chlorophenyl, fluorophenyl, dichlorophenyl, trifluoromethylphenyl;

$R^2$ = hydrogen; optionally substituted lower alkyl of a maximum of 6 carbon atoms, e.g., methyl, ethyl, isopropyl, chloromethyl; aryl, e.g., phenyl; and halogen, e.g., chloro, bromo, iodo;

$R^3$ and $R^4$ = hydrogen, and lower alkyl, especially methyl;

$R^5$ and $R^6$ = lower alkyl of a maximum of 6 carbon atoms, e.g., methyl, ethyl, n-propyl, isopropyl, n-butyl, sec-butyl, isobutyl, n-pentyl, 2-pentyl, 3-pentyl, n-hexyl; lower alkenyl of a maximum of 4 carbon atoms, e.g., allyl, methallyl, but-2-en-1-yl, but-4-en-1-yl; cycloalkyl of a maximum of 8 carbon atoms optionally substituted by lower alkyl, e.g., cyclopropyl, cyclobutyl, cyclopentyl, cyclohexyl, 2-methylcyclopentyl; alkoxyalkyl of a maximum of 6 carbon atoms, e.g., 2-methoxyethyl, 2-ethoxyethyl, 1-methoxy-2-propyl, 3-methoxypropyl; haloalkyl of a maximum of 4 carbon atoms, e.g., 2-chloroethyl, 1-chloro-2-propyl, 3-chloropropyl; $R^5$ and $R^6$ together with the nitrogen atom may also denote a heterocyclic ring of a maximum of 10 carbon atoms optionally substituted by one or more lower alkyl groups, e.g., azetidine, 2-methylazetidine, 2,4-dimethylazetidine, 2,4,4-trimethylazetidine, pyrrolidine, 2-methylpyrrolidine, 2-ethylpyrrolidine, 2,5-dimethylpyrrolidine, piperidine, 2-methylpiperidine, 2-ethylpiperidine, 2-methyl-5-ethylpiperidine, hexahydroazepine, 2-methylhexahydroazepine, 2,3-dimethylhexahydroazepine, heptamethylenimine, bicyclo-[3,2,2]-3-azanonane, morpholine, 2,6-dimethylmorpholine, 3,5-dimethylmorpholine.

The compounds according to the invention of the formula I may be prepared in accordance with the equation below by reaction of an isoxazolyl methyl halide or isoxazolyl methylalkane sulfonate with a salt of a thiol carbamate.

Process A:

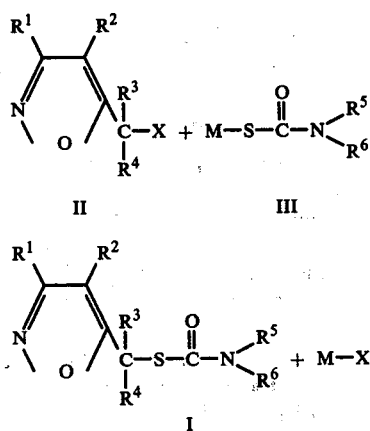

$R^1$ to $R^6$ have the abovementioned meanings; X denotes halogen or alkane sulfonate and M an alkali metal atom or ammonium optionally substituted by 2 or 3 alkyls. The starting materials of the formula II employed in process A are known or may be prepared by reaction of nitrile oxides with acetylene halides. Examples of such compounds are 5-chloromethyl-3-methylisoxazole, 5-bromomethyl-3-ethylisoxazole, 5-chloromethyl-3-isopropylisoxazole, 5-bromomethyl-3-tert-butylisoxazole, 5-chloromethyl-3,4-dimethylisoxazole, 5-(1'-chloroethyl)-3-methylisoxazole, 5-bromomethyl-3-phenylisoxazole, 5-chloromethyl-3-(3',4'-dichlorophenyl)-isoxazole, and 5-bromomethyl-3-cyclohexylisoxazole. The compounds 5-chloromethylisoxazole and 5-bromomethyl-3-methyl-4-chloro (or 4-bromo)-isoxazole are known from the literature (Kochetkow and coworkers, Chemical Abstracts, 47, 2167, 1953; Khim. Geterotsikl. Soedin., 1974, 602). The corresponding isoxazolyl methylalkane sulfonates may be prepared from prior art isoxazolyl methanols (Gass. chim. ital., 69, 536, 1939) in conventional manner by reaction with alkanesulfonic acid chlorides in the presence of agents which bind hydrogen chloride, e.g., pyridine. The isoxazolyl methyl halides may for instance be prepared as follows:

Specification A1

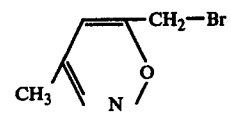

238 g (parts by weight) of propargyl bromide, 476 g (parts by weight) of phenyl isocyanate and 158 g (parts by weight) of nitroethane are dissolved in 1500 ml of toluene; at 15° to 20° C., 1 ml of triethylamine (to activate the phenyl isocyanate) is added. The temperature is kept at from 15° to 30° C. for 3 hours, and 1 ml of triethylamine (4 ml in all) is added each hour. The mixture is then stirred for 1 hour at 70° C. and then cooled. The precipitate is suction filtered and the residue rinsed with 1 l of toluene. The combined filtrates are concentrated and the residue is distilled under an oil pump vacuum. At 59° to 61° C./0.2 mm Hg, 310 g ($\approx$ 88% of theory) of 3-bromomethyl-5-methylisoxazole distils over ($n_D^{25}$: 1.5168).

| | $C_5H_6BrNO$ (176) | | | |
|---|---|---|---|---|
| | C | H | N | Br |
| Calc.: | 34.2 | 3.4 | 7.9 | 45.5 |
| Found: | 34.0 | 3.4 | 8.0 | 45.4 |

60 MHz nmr spectrum (CDCl$_3$; δ values) 2.3 (3H, s), 4.44 (2H,s), 6.15 (1H, s)

13 C nmr spectrum (CDCl$_3$, ppm values relative to TMS):
167.2 (C), 160.1 (C), 104.5 (CH), 18.8 (CH$_2$), 11.3 (CH$_3$).

Specification A2

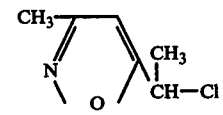

93.5 g (parts by weight) of acetohydroximoyl chloride (Ber. dtsch. chem. Ges., 40, 1677, 1907) and 90 g (parts by weight) of isobutynyl chloride are stirred in 1500 ml of benzene; at 15° to 20° C., 105 g (parts by weight) of triethylamine is added dropwise. The mixture is then stirred for 1 hour at from 20° to 25° C. and for 1 hour at 70° C. After the mixture has been allowed to cool it is filtered and the filtrate concentrated. The distillate which remains is distilled under an oil pump vacuum. There is obtained 133 g (92% of theory), b.p. 48° to 50° C./0.05 mm Hg; $n_D^{25}$: 1.4740.

|  | $C_6H_8NOCl$ (145.5) | | | |
|---|---|---|---|---|
|  | C | H | N | Cl |
| Calc.: | 49.6 | 5.5 | 9.7 | 24.5 |
| Found: | 49.5 | 5.7 | 10.0 | 24.0 |

60 MHz nmr spectrum (CDCl$_3$, δ values): 1.78 (d, 3H), 2.3 (s, 3H), 5.05 (9, 1H), 6.09 (s, 1H).
13 C nmr spectrum (CDCl$_3$, ppm values relative to TMS):
171.5 (C), 159.8 (C), 102.5 (CH), 47.4 (CH), 23.3 (CH$_3$), 11.5 (CH$_3$).

Specification A3

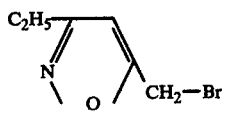

119 g (parts by weight) of propargyl bromide, 95 g (parts by weight) of nitropropane and 440 g (parts by weight) of triethylamine are dissolved in 1200 ml of chloroform; at 0° C., 155 g (parts by weight) of phosphoroxy chloride is added dropwise. The mixture is kept at 20° C. for 30 minutes and refluxed for 2 hours. After the mixture has been cooled, filtration and concentration are carried out, and the residue is taken up in water. The water phase is extracted several times with toluene and the combined toluene phases are washed with water and subsequently dried over sodium sulfate. The sodium sulfate is then separated and the filtrate concentrated; the residue is distilled under an oil pump vacuum. At 78° to 79° C./0.1 mm Hg, 150 g (79% of theory) distil off; $n_D^{25}$: 1.5108.

|  | $C_6H_8BrNO$ (190) | | | |
|---|---|---|---|---|
|  | C | H | N | Br |
| Calc.: | 37.9 | 4.7 | 7.4 | 42.0 |
| Found: | 38.0 | 4.6 | 7.6 | 41.7 |

The following compounds are obtained analogously:

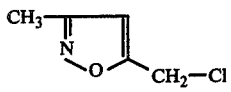 $n_D^{25} = 1.4806$

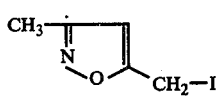 $n_D^{25} = 1.5500$

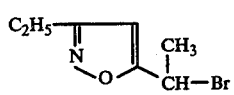

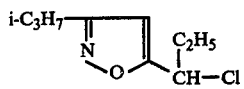

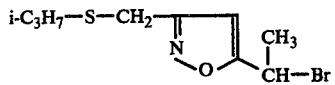

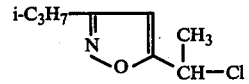

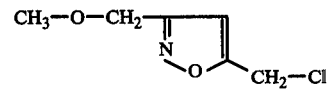

The compounds designated with formula III are salts of thiolcarbamic acids. Typical representatives, which may be prepared in conventional manner, are the sodium salts or the ammonium salts — optionally substituted by 2 or 3 alkyls — of N,N-dimethylthiolcarbamic acid, N,N-diethylthiolcarbamic acid, N,N-diisopropylthiolcarbamic acid, N,N-di-n-propylthiolcarbamic acid, N,N-di-n-butylthiolcarbamic acid, N,N-diisobutylthiolcarbamic acid, N-ethyl-N-n-butylthiolcarbamic acid, N-ethyl-N-isopropylthiolcarbamic acid, N-ethyl-N-cyclohexylthiolcarbamic acid, N,N-diallylthiolcarbamic acid, further N-azetidine-, N-pyrrolidine-, N-piperidine- and N-hexahydroazepinethiolcarbamic acid and their derivatives substituted in the ring by 1 to 3 methyl and/or ethyl groups.

Process A may be carried out in the presence of any inert organic solvents, for instance hydrocarbons, e.g., cyclohexane, benzene, toluene; halogenated hydrocarbons, e.g., methylene chloride, chloroform, carbon tetrachloride, chlorobenzene; ethers, e.g., diethyl ether, diisopropyl ether, tetrahydrofuran, dioxane, glycol dimethyl ether; lower alcohols and ketones, e.g., methanol, ethanol, isopropanol, acetone, methyl ethyl ketone, cyclohexanone; nitriles, e.g., acetonitrile; and water. Mixture of these solvents may also be used.

For the preparation of the new active ingredients, process A is preferred.

If desired, the isoxazolylmethylthiol carbamates of the formula I according to the invention may also be prepared in accordance with process B by reaction of isoxazolylmethyl mercaptans or their salts with carbamic acid chlorides.

Process B

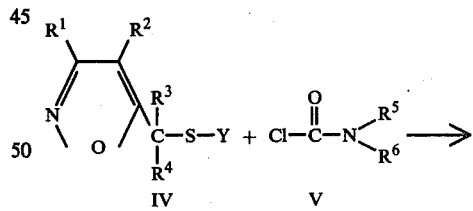

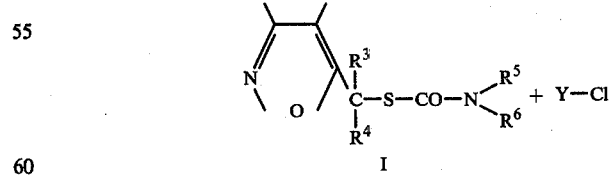

In the formulae, $R^1$ to $R^6$ have the above meanings and Y denotes hydrogen, an alkali metal atom, or ammonium optionally substituted by 2 or 3 alkyls.

Formula IV represents starting materials which may be prepared by conventional methods from the isoxazolyl methyl halides of the formula II by reaction with hydrogen sulfide or salts thereof (e.g., Houben-Weyl, Methoden der Organischen Chemie, IX, 1–18). The following are examples of mercaptans of the formula IV: 3-methylisoxazolyl-5-methylmercaptan, 3-ethylisoxazolyl-5-methylmercaptan, 3-phenylisoxazolyl-5-methylmercaptan, 3-methylisoxazolyl-5-(1'-ethyl)-mercaptan.

Examples of carbamoyl chlorides of the formula V are those of dimethylamine, diethylethylamine, di-n-propylamine, diisopropylamine, di-n-butylamine, N-ethyl-n-butylamine, N-ethyl-n-isopropylamine, azetidine, pyrrolidine, piperidine, hexahydroazepine and derivatives thereof substituted on the ring by 1 to 3 methyl and/or ethyl groups.

Process B is expediently carried out in the presence of a hydrogen chloride acceptor. Suitable for this purpose are any inorganic bases, e.g., alkali metal bicarbonates, carbonates and hydroxides; organic bases, such as alkali metal alcoholates, e.g., sodium methylate; tertiary amines, e.g., triethylamine and N,N-dimethylcyclohexylamine; and saturated or unsaturated nitrogen heterocycles, e.g. N-methylpiperidine, pyridine and quinoline. The process is advantageously carried out using one of the solvents (or mixtures thereof) listed at process A.

The isoxazolylmethylthiol carbamates of the invention of the formula I may also be prepared by reaction of an isoxazolylmethylthiochlorocarbonic acid ester with a secondary amine.

Process C:

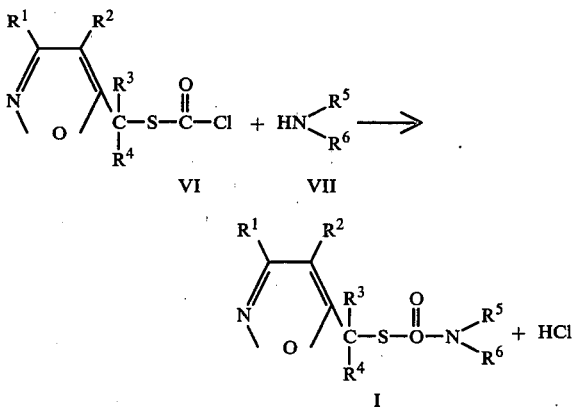

In the formulae, $R^1$ to $R^6$ have the abovementioned meanings.

The thiochlorocarbonic acid esters of the formula VI may be prepared in conventional manner from the isoxazolylmethylmercaptans of the formula IV (Y = hydrogen) and phosgene. Examples of compounds of the formula VI are 3-methylisoxazolyl-5-methylthiocarbonyl chloride, 3-ethylisoxazolyl-5-methylthiocarbonyl chloride, and 3-phenylisoxazolyl-5-methylthiocarbonyl chloride. Suitable secondary amines of the formula VII are particularly those listed at process B as components of the carbamic acid chlorides. Process C may be carried out using the inert solvents mentioned in process A — less advantageously in alcohols or water — and with or without the addition of one of the hydrogen chloride acceptors mentioned in process B.

In detail, process A may for instance be carried out as follows

At from $-20°$ to $+50°$ C., 1 mole of an isoxazolylmethyl halide or alkane sulfonate of the formula II, optionally in one of the above solvents, is dripped into a solution or suspension of at least 1 mole of a thiol carbamate of the formula III. To complete the reaction, the mixture is stirred for from 3 to 12 hours at from 0° to to 80° C. Upon completion of the reaction, the mixture is poured into water and the product is extracted, if desired with an inorganic solvent immiscible with water, and subsequently isolated by distillation or crystallization.

Process B may for instance be carried out in the following manner.

A solution of 1 mole of isoxazolylmethylmercaptan of the formula IV in a solvent is reacted with at least one mole of a carbamic acid chloride of the formula V in the presence of at leat 1 mole of one of the abvementioned inorganic or organic bases at from $-10°$ to $+80°$ C. and for from 1 to 12 hours. The thiol carbamates according to the invention of the formula I are isolated as described above.

Process C is for instance carried out as follows.

A solution of 1 mole of a thiochlorocarbonic acid ester of the formula VI in an inert organic solvent is reacted with at least 1 mole of an amine of the formula VII; the acid-binding agent may be at least 1 mole of the inorganic or organic bases mentioned in process B. The reaction temperature is from $-10°$ to $+80°$ C. and the reaction time from 1 to 12 hours, as in process B, depending on the reactants, the base and the solvent employed. The thiol carbamates are isolated as described above.

The following examples, in which the parts are by weight, illustrate the processes for preparing the isoxazolylmethylthiol carbamates according to the invention of the formula I.

EXAMPLE 1

At 0° C., 60.0 parts of carbonyl sulfide was gassed into a mixture of 102 parts of N-ethylcyclohexylamine, 80.8 parts of triethylamine and 700 parts of methylene chloride, and the whole was stirred for 2 hours at room temperature. Subsequently, 105.3 parts of 3-methyl-5-chloromethylisoxazole was dripped in over a period of 1 hour at 0° C., and the mixture stirred for 10 hours at room temperature. The salt which had formed was filtered off and the filtrate was washed successively with water, 1N hydrochloric acid and again with water, and dried. After removal of the solvent, distillation of the residue gave 194.2 parts of 3-methyl-5-isoxazolylmethyl-N-ethyl-N-cyclohexylthiol carbamate, b.p. (0.2 mm Hg) 176°–179° C. (m.p. 60°–62° C.).

EXAMPLE 2

At 0° C., 8.0 parts of carbonyl sulfide was gassed into a mixture of 21.2 parts of diisopropylamine in 100 parts of toluene, and the whole stirred for 30 minutes at 0° C. and for 1 hour at room temperature. Subsequently, 19.0 parts of 3-ethyl-5-bromomethylisoxazole was dripped in over a period of 15 minutes and the whole stirred for 3 hours at room temperature. After working up as in Example 1, there was obtained 21.8 parts of 3-ethyl-5-isoxazolylmethyl-N,N-diisopropylthiol carbamate having a boiling point at 0.3 mm Hg of 154°–156° C. ($n_D^{25}$: 1.5089).

EXAMPLE 3

While cooling, 29.8 parts of N,N-diethylcarbamic acid chloride was dripped into a mixture of 25.8 parts of 3-methylisoxazolyl-5-methylmercaptan in 100 parts of ether and 50 parts of pyridine; the whole was then refluxed for 3 hours. After working up as in Example 1, there was obtained 35.8 parts of 3-methyl-5-isoxazolyl-methyl-N,N-diethylthiol carbamate having a boiling point at 0.05 mm Hg of 136°–138° C.

The following isoxazolylmethylthiol carbamates according to the invention may be prepared by one of the abovementioned processes.

| No. | R¹ | R² | R³ | R⁴ | R⁵ | R⁶ | Phys. data (b.p./mm Hg; m.p.; n$_D^{25}$) |
|---|---|---|---|---|---|---|---|
| 3 | CH₃ | H | H | H | C₂H₅ | C₂H₅ | Example 3 |
| 4 | CH₃ | H | H | H | i-C₃H₇ | i-C₃H₇ | 143/0.05 (68° C) |
| 5 | CH₃ | H | H | H | —(CH₂)₆— | | n$_D^{25}$ 1.5435 |
| 6 | CH₃ | H | CH₃ | H | C₂H₅ | C₂H₅ | 124/0.05 |
| 7 | CH₃ | H | CH₃ | H | i-C₃H₇ | i-C₃H₇ | 132/0.05 |
| 8 | CH₃ | H | CH₃ | H | —(CH₂)₆— | | 160/0.2 |
| 9 | CH₃ | H | H | H | n-C₃H₇ | n-C₃H₇ | 139/0.5 |
| 2 | C₂H₅ | H | H | H | i-C₃H₇ | i-C₃H₇ | Example 2 |
| 10 | CH₃ | H | H | H | CH₂—CH(CH₃)₂ | CH₂—CH(CH₃)₂ | 143/0.05 |
| 11 | CH₃ | H | H | H | n-C₄H₉ | n-C₄H₉ | 164/0.2 |
| 12 | CH₃ | H | H | H | CH₂—CH=CH₂ | CH₂—CH=CH₂ | 144/0.2 |
| 1 | CH₃ | H | H | H | C₂H₅ | cyclo-C₆H₁₁ | Example 1 |
| 13 | CH₃ | H | H | H | C₂H₅ | n-C₄H₉ | 147/0.3 |
| 14 | CH₃ | H | H | H | —(CH₂)₅—CH(CH₃)— | | 170/0.4 |
| 15 | CH₃ | H | H | H | —(CH₂)₃— | | m.p. 72–73° C |
| 16 | CH₃ | H | H | H | —CH(CH₃)—CH₂—C(CH₃)₂— | | 148/0.2 |
| 17 | CH₃ | H | H | H | —CH(CH₃)—CH(CH₃)—(CH₂)₄— | | 184/0.4 |
| 18 | Cl—⌬(O)—, Cl | H | H | H | C₂H₅ | C₂H₅ | m.p. 88–90° C |
| 19 | Cl—⌬(O)—, Cl | H | H | H | i-C₃H₇ | i-C₃H₇ | m.p. 99–101° C |
| 20 | C₂H₅ | H | H | H | C₂H₅ | C₂H₅ | 144/0.1 |
| 21 | C₂H₅ | H | H | H | n-C₃H₇ | n-C₃H₇ | 152/0.2 |
| 22 | C₂H₅ | H | H | H | —(CH₂)₆— | | 180/0.3 |
| 23 | C₂H₅ | H | H | H | —CH(CH₃)—(CH₂)₅— | | 184/0.3 |
| 24 | C₂H₅ | H | H | H | —CH(CH₃)—CH(CH₃)—(CH₂)₄— | | 190/0.2 |
| 25 | C₂H₅ | H | H | H | n-C₄H₉ | n-C₄H₉ | 168/0.1 |
| 26 | C₂H₅ | H | H | H | —CH(CH₃)—CH₂—C(CH₃)₂— | | 139/0.05 |
| 27 | C₂H₅ | H | H | H | C₂H₅ | n-C₄H₉ | 154/0.1 |
| 28 | C₂H₅ | H | H | H | —CH(C₂H₅)—(CH₂)₄— | | 170/0.1 |
| 29 | C₂H₅ | H | H | H | —CH(CH₃)—(CH₂)₄— | | 165/0.2 |
| 30 | C₂H₅ | H | H | H | —CH(CH₃)—(CH₂)₃— | | 166/0.1 |
| 31 | C₂H₅ | H | H | H | C₂H₅ | cyclo-C₆H₁₁ | 180/0.1 |
| 32 | CH₃ | H | H | H | C₂H₅ | i-C₃H₇ | 124/0.04 |
| 33 | CH₃ | H | H | H | CH₂CH₂OCH₃ | CH₂CH₂OCH₃ | 200/0.04 |
| 34 | CH₃ | H | CH₃ | H | —CH(CH₃)—CH₂—C(CH₃)₂— | | 136/0.1 |
| 35 | CH₃ | H | CH₃ | H | —CH(CH₃)—(CH₂)₅— | | 167/0.01 |
| 36 | CH₃ | H | CH₃ | H | —CH(CH₃)—CH(CH₃)—(CH₂)₄— | | 157/0.01 |
| 37 | CH₃ | H | H | H | —(CH₂)₂—O—(CH₂)₂— | | m.p. 74–76° C |
| 38 | CH₃ | H | H | H | CH₂—CH(CH₃)₂ | CH—CH₂—CH₃ \| CH₃ | 152/0.2 |
| 39 | CH₃ | Cl | H | H | CH(CH₃)₂ | CH(CH₃)₂ | 148/0.2 |
| 40 | CH(CH₃)₂ | H | H | H | CH(CH₃)₂ | CH(CH₃)₂ | 148/0.2 |
| 41 | C₂H₅ | H | H | H | CH₂CH=CH₂ | cyclo-C₆H₁₁ | 187/0.1 |
| 42 | C₂H₅ | H | H | H | CH(CH₃)₂ | CH₂—CH(CH₃)₂ | 153/0.1 |
| 43 | C(CH₃)₃ | H | H | H | CH(CH₃)₂ | CH(CH₃)₂ | 144/0.2 |
| 44 | C(CH₃)₃ | H | H | H | C₂H₅ | cyclo-C₆H₁₁ | 168/0.1 |
| 45 | C(CH₃)₃ | H | H | H | —CH(CH₃)—CH₂—C(CH₃)₂— | | 142/0.1 |
| 46 | C(CH₃)₃ | H | H | H | C₂H₅ | n-C₄H₉ | 152/0.1 |
| 47 | CH₃ | Cl | H | H | C₂H₅ | cyclo-C₆H₁₁ | 178/0.2 |
| 48 | CH₃ | Cl | H | H | C₂H₅ | n-C₄H₉ | 157/0.2 |
| 49 | CH₃ | Cl | H | H | —CH(CH₃)—CH₂—C(CH₃)₂— | | 147/0.2 |
| 50 | CH₃ | Cl | H | H | —CH(CH₃)—CH(CH₃)—(CH₂)₄— | | 180/0.2 |
| 51 | CH₃ | H | CH₃ | H | n-C₃H₇ | n-C₃H₇ | 156/0.1 |
| 52 | CH₃ | H | CH₃ | H | CH₂CH(CH₃)₂ | CH₂—CH(CH₃)₂ | 157/0.2 |
| 53 | CH₃ | H | CH₃ | H | CH₂—CH=CH₂ | CH₂—CH=CH₂ | 150/0.1 |
| 54 | CH₃ | H | CH₃ | H | C₂H₅ | n-C₄H₉ | 148/0.1 |
| 55 | CH₃ | H | CH₃ | H | CH(CH₃)₂ | CH₂—CH(CH₃)₂ | 142/0.1 |
| 56 | C₂H₅ | H | CH₃ | H | CH(CH₃)₂ | CH(CH₃)₂ | 148/0.1 |
| 57 | C₂H₅ | H | CH₃ | H | C₂H₅ | cyclo-C₆H₁₁ | 170/0.1 |
| 58 | C₂H₅ | H | CH₃ | H | C₂H₅ | n-C₄H₉ | 143/0.1 |
| 59 | C₂H₅ | H | CH₃ | H | CH(CH₃)₂ | CH₂—CH(CH₃)₂ | 146/0.1 |
| 60 | C₂H₅ | H | CH₃ | H | CH₂—CH(CH₃)₂ | CH(CH₃)-CH₂-CH₃ | 142/0.08 |
| 61 | CH(CH₃)₂ | H | CH₃ | H | C₂H₅ | cyclo-C₆H₁₁ | 184/0.1 |
| 62 | CH(CH₃)₂ | H | CH₃ | H | CH(CH₃)₂ | CH(CH₃)₂ | oil |
| 63 | C(CH₃)₃ | H | CH₃ | H | CH(CH₃)₂ | CH(CH₃)₂ | 90° C |
| 64 | ⌬(O)— | H | H · | H | CH(CH₃)₂ | CH(CH₃)₂ | 104° C |
| 65 | CH(CH₃)₂ | H | CH₃ | H | C₂H₅ | n-C₄H₉ | 164/0.1 |
| 66 | C(CH₃)₃ | H | CH₃ | H | C₂H₅ | n-C₄H₉ | 165/0.2 |
| 67 | C(CH₃)₃ | H | CH₃ | H | C₂H₅ | cyclo-C₆H₁₁ | 73° C |
| 68 | C(CH₃)₃ | H | CH₃ | H | CH₂—CH(CH₃)₂ | CH(CH₃)-CH₂-CH₃ | 172/0.1 |
| 69 | CH₃ | H | CH₃ | H | —CH₂—CH₂—CH₂—CH—CH(CH₃)— | | 76° C |
| 70 | CH₃ | H | CH₃ | H | —CH₂—CH₂—CH₂—CH(CH₃)— | | 140/0.01 |
| 71 | CH₃ | H | CH₃ | H | —CH₂—CH₂—CH₂—CH(C₂H₅)— | | 1.5297 |
| 72 | C₂H₅ | H | CH₃ | H | —CH(CH₃)—CH₂—C(CH₃)₂— | | 1.5129 |
| 73 | CH₃ | H | CH₃ | H | —CH₂—CH₂—CH=CH—CH₂— | | 46–47° C |

| No. | R¹ | R² | R³ | R⁴ | R⁵ | R⁶ | Phys. data (b.p./mm Hg; m.p.; $n_D^{20}$) |
|---|---|---|---|---|---|---|---|
| 74 | CH₃ | | H | CH₃ | H | | 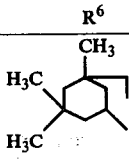 | 1.5258 |
| 75 | CH₃ | | H | CH₃ | H | |  | 1.5502 |

EXAMPLES DEMONSTRATING THE HERBICIDAL ACTION OF THE NEW ISOXAZOLYLMETHYLTHIOL CARBAMATES

A series of experiments, divided in the main into the following three groups, was carried out to provide evidence in support of the statements made in the introduction about these active ingredients.

I. Greenhouse experiments

The vessels employed were paraffined paper cups having a volume of 200 cm³, and the substrate was a sandy loam containing about 1.5% (wt%) humus. The seeds of the test plants were sown shallow and separated according to species. The active ingredients were applied immediately (preemergence treatment), suspended or emulsified in water as the distribution medium and sprayed onto the soil surface by means of finely distributing nozzles. Prior to the chemical treatment, the cups were lightly sprinkler-irrigated; the agents therefore came into contact with moist soil. After application of the agents the vessels were covered with transparent plastic hoods until the plants had taken root. This cover prevented the evaporation of water and readily volatile substances. Another effect was the more uniform emergence of the test plants, to the extent that they were not impaired by chemicals. When postemergence treatment was employed, the plants were first grown in the vessels to a height of from 3 to 10 cm, depending on the form of growth, and then treated. A cover was not used. Depending on the temperature requirements of the plants, the experiments were set up either in the cooler (10°-20° C.) or warmer (18°-30° C.) portion of the greenhouse. The experiments lasted for from 2½ to 6 weeks. During this period, the plants were tended and their reaction to the individual treatment was evaluated. The substances examined, the dose rates employed (in kg/ha of active ingredient) and the types of plant used in the experiments are given in the following tables. A 0–100 scale was used for assessment, 0 denoting no damage or normal emergence, and 100 denoting complete destruction or non-emergence.

II. Experiments in the open

These experiments were carried out on small plots of various sizes. The soil was a sandy loam having a pH of 5–6 and 1–1.5% humus. The compounds were applied from early to late fall and from early to late spring, corresponding to the sowing period for the crop plants. The compounds were emulsified or suspended in water as carrier and distribution medium, and applied by means of a motor-driven plot spray mounted on a hitch. The application methods most frequently employed were preplant incorporation and preemergence surface application. In individual experiments, the action of the agents when sprayed during emergence of the crop plants and weeds, and postemergence after formation of a few genuine leaves was examined. All the experiments were run for several months; during this period assessments were made at certain intervals employing the 0 to 100 scale.

III. Herbicidal action via the vapor phase

The remarkable herbicidal action of isoxazolylmethylthiol carbamates, even when not incorporated into the soil as is necessary with prior art thiol carbamates, suggested that the losses of active ingredient through evaporation were low. To examine this, the following experiment was carried out in the greenhouse. Seeds of a sensitive oat crop were sown as described in Section I (greenhouse experiments) and treated with the herbicidal active ingredients at various rates. The vessels were not however covered with a plastic hood, but placed in pairs in 5 liter glass cylinders. The pairs were made up of a treated and an untreated vessel. For comparison purposes, control cylinders containing only untreated pots were used. To prevent gas exchange with the atmosphere, the rims of the cylinders were coated with Vaseline and the opening was covered with a glass plate. Readily evaporating substances were thus able to escape from the surface of the soil in the vessels into the cylinder space and possibly influence the germination and development of the test plants in the parallel vessels originally free from active ingredient. The temperature in the glass cylinders varied from 11° C. in the morning to 30° C. in the afternoon in sunlight. After 14 days, the plants in the control cylinders had reached a height of from 13 to 15 cm and the differences between the various treatments were readily perceptible. In addition to a visual assessment, the green weight of the oat shoots was determined for each vessel. This is given in Table 11.

Results

The individual results from the various experiments and tables combine to give the following picture.

(1) The introduction of the isoxazolylmethyl radical into the thiol carbamates resulted in a shift in action, particularly in a broadening of the range of action compared with prior art thiol carbamates. Thus, for instance, some compounds developed an activity embracing that of N,N-diisopropylthiol-2,3-dichloroallyl carbamate or N,N-diisopropylthiol-2,3,3-trichloroallyl carbamate and of N,N-dipropylthiolethyl carbamate (cf. Tables 2, 3 and 5). In other instances, a similar, at times somewhat poorer, herbicidal performance to that N-ethyl-N-cyclohexylthiolethyl carbamate was found. However, the selectivity range in crop plants was incomparably greater (cf. Table 6). It should be pointed out at this juncture that the prior art thiol carbamates were only employed in the experiments because of their action as herbicides. Compounds having a structure similar to that of the compounds of the invention are hitherto unknown. A thiol carbamate having a heterocyclic ring and known as a herbicide had insignificant activity (Table 3). The corresponding dithiol carbamate was completely ineffective. Table 4 contains a further example of the herbicidal action of the new isoxazolylmethylthiol carbamates.

(2) Whereas prior art thiol carbamates can only be used in specific crop plants or groups thereof (e.g., broadleaved species) because of (a) their phytotoxicity, (b), incorporation necessary for herbicidal action, and (c) the weed spectrum combatted, some of the new compounds have an improved and wider selectivity (Tables 3, 5, 6 and 7). Plant physiology may provide an explanation for the selectivity of the compounds of the invention; the selectivity may also be attributable in part to the application method employed. Immobile substances distributed on the surface of the soil do not come into contact in phytotoxic amounts with the seeds and roots of the crop plants lying somewhat deeper. This selectivity is apparent in the case of compounds which can be left on the surface of the soil after application, but does not exist when the active ingredients have to be incorporated into the soil because of their high vapor pressure or for other reasons, in order to avoid evaporation losses.

(3) The new compounds according to the invention had, when incorporated before sowing, an action similar to that of prior art compounds. When applied without incorporation they were superior to the prior art thiol carbamates suitable for the crop in question (Table 8). Remarkable in this connection is the fact that for instance the compound 3-methyl-5-isoxazolylmethyl-N,N-diisopropylthiol carbamate, when applied preemergence to the surface, combatted unwanted plants in Indian corn just as well as significant prior art preemergence herbicides of different structure (Table 9). Successful control was also obtained during and after emergence of the unwanted plants; the crop plants remained unaffected (Tables 8, 10).

(4) The phytotoxicity of the vapors of N,N-diisopropylthiol-2,3,3-trichloroallyl carbamate for wild oats is known. This was confirmed in model experiments. Of the new compounds, it was found that for instance the substance 3-methyl-5-isoxazolylmethyl-N,N-diisopropylthiol carbamate had just as aggressive an action on the crop plant oats in the directly treated vessels as N,N-diisopropylthiol-2,3-dichloroallyl carbamate or N,N-diisopropylthiol-2,3,3-trichloroallyl carbamate. The plants in the untreated pots located in the same glass cylinder remained undamaged by this new compound, whereas plant growth in the case of the comparative compound had suffered (Table 11). Consequently, not enough active ingredient had escaped from the directly treated pots to cause damage, via the gas phase, to the neighboring test plants. The actual vapor pressure of 3-methyl-5-isoxazolylmethyl-N,N-diisopropylthiol carbamate was $1.3 \times 10^{-5}$ mbar at 20° C., whereas that of N,N-diisopropylthiol-2,3-dichloroallyl carbamate at the same temperature was $3.7 \times 10^{-4}$ mbar.

It goes without saying that the experimental results discussed here are only examples of the reaction of numerous unwanted and crop plants from a wide variety of botanical families. The application rates too can be varied beyond the examples; they depend on the end to which they are applied and on local conditions (site, plant size), and may for instance vary from 0.1 to 10 kg of active ingredient per hectare.

The particular advantage of this new group of isoxazolylmethylthiol carbamates over prior art thiol carbamates is the range of possible application methods.

Table 1

| List of plants used in the experiments | | |
|---|---|---|
| Latin name | Abbreviation in tables | English term |
| Alopecurus myosuroides | Alopec. myosur. | slender foxtail |
| Amaranthus retroflexus | Amar. retro. | pigweed |
| Avena fatua | Avena fat. | wild oat |
| Beta vulgaris | Beta vulg. | sugar beet |
| Brassica napus | | rape |
| Chenopodium album | | lambsquarter |
| Cynodon dactylon | Cynod. dactyl. | Bermudagrass |
| Cyperus esculentus | Cyper. escul. | yellow nutsedge |
| Echinochloa grus galli | Echin. e.g. | barnyardgrass |
| Eleusine indica | Eleus. ind. | goosegrass |
| Euphorbia geniculata | Euph. genic. | South American member of the spurge family |
| Glycine max | | soybeans |
| Gossypium hirsutum | Gossyp. hirs. | cotton |
| Hordeum vulgare | | barley |
| Lolium multiflorum | Lolium multifl. | Italian ryegrass |
| Matricaria spp. | Matric. spp. | chamomile |
| Poa annua | | annual bluegrass |
| Setaria faberii | Set. fab. | giant foxtail |
| Setaria spp. | | foxtail spp. |
| Solanum nigrum | | black nightshade |
| Sorghum halepense | Sorgh. halep. | johnsongrass |
| Stellaria media | | chickweed |
| Triticum aestivum | Tritic. aest. | wheat |
| Zea mays | | Indian corn |

Table 2

Action on important weed grasses in the greenhouse; preemergence treatment

Basic molecule $\overset{R^1}{\underset{R^2}{\diagup}} N-\underset{\underset{O}{\parallel}}{C}-S-R^3$

| Substituents in the substances examined | | | Compound no. | Application rate kg/ha | Test plants and % damage | | |
|---|---|---|---|---|---|---|---|
| $R^1$ | $R^2$ | $R^3$ | | | Alopecurus myosuroides | Avena fatua | Echinochloa crus galli |
| | | | 6 | 0.75 | 60 | — | 80 |
| | | | | 1.5 | 90 | — | 90 |
| | | | | 3.0 | 100 | — | 90 |
| | | | 3 | 0.75 | 95 | 0 | 60 |
| | | | | 1.5 | 100 | 80 | 70 |
| | | | | 3.0 | 100 | 80 | 75 |
| | | | 4 | 0.75 | 90 | 65 | 85 |
| | | | | 1.5 | 95 | 95 | 90 |
| | | | | 3.0 | 95 | 100 | 95 |
| $C_2H_5$ | $C_2H_5$ | $CH_2\text{—}\langle\text{—}\rangle\text{—}Cl$ | prior art | 0.75 | 90 | 0 | 95 |
| | | | | 1.5 | 95 | 80 | 95 |
| | | | | 3.0 | 95 | 80 | 95 |

Table 2-continued

| | | | | Application rate kg/ha | | | |
|---|---|---|---|---|---|---|---|
| C$_3$H$_7$n | C$_3$H$_7$n | C$_2$H$_5$ | prior art | 0.75 | 40 | 80 | 0 |
| | | | | 1.5 | 90 | 90 | 20 |
| | | | | 3.0 | 95 | 95 | 70 |

| | Application | Test plants and % damage | | |
|---|---|---|---|---|
| Compound no | rate kg/ha | Alopecurus myosurides | Avena fatua | Echinochloa crus galli |
| 34 | 2.0 | 94 | 98 | 94 |
| 39 | 2.0 | 95 | 92 | 80 |
| | 4.0 | 100 | 100 | 78 |
| 40 | 1.0 | 80 | 95 | 90 |
| | 2.0 | 90 | 95 | 95 |
| 23 | 2.0 | 80 | 80 | 90 |
| | 4.0 | 100 | 100 | 95 |
| 24 | 2.0 | 90 | 60 | 85 |
| | 4.0 | 100 | 100 | 90 |

0 = no damage
100 = complete destruction

Table 3

Removal of unwanted plants by, and tolerance of crop plants to, thiol carbamates in the greenhouse; preemergence treatment Basic molecule
$$\begin{array}{c} R^1 \\ \diagdown \\ N-C-S-R^3 \\ \diagup \; \| \\ R^2 \; O \end{array}$$

| Substituents in the substances examined | | | | | Test plants and % damage | | | | | |
|---|---|---|---|---|---|---|---|---|---|---|
| R$^1$ | R$^2$ | R$^3$ | Compound no. | Appl. rate kg/ha | Brassica napus | Glycine max | Gossy. hirs. | Zea mays | Alopec myosur. | Amar. retro. | Cyperus escul. |
| CH(CH$_3$)$_2$ | CH(CH$_3$)$_2$ | 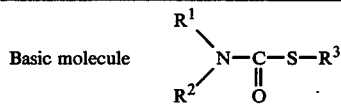 | prior art | 1,0 | 0 | 20 | — | 0 | 0 | 0 | — |
| | | | | 4,0 | 0 | 90 | — | 25 | 90 | 20 | — |
| (FR-PS 2 205 514) | | | | | | | | | | | |
| | | | | 1.0 | 0 | 0 | 10 | 0 | 100 | 100 | 42 |
| | | | 4 | 2.0 | 0 | 5 | 20 | 10 | 100 | 100 | 85 |
| | | | | 4.0 | 0 | 15 | 27 | 10 | 100 | 100 | 85 |
| | | | | 1.0 | 0 | 0 | 0 | 0 | 100 | 100 | 60 |
| | | | 2 | 2.0 | 0 | 5 | 0 | 0 | 100 | 100 | 60 |
| | | | | 4.0 | 0 | 15 | 5 | — | 100 | 100 | 82 |
| | | | | 1.0 | 0 | 0 | 20 | 0 | 80 | 100 | 30 |
| | | | 9 | 2.0 | 0 | 0 | 25 | 0 | 100 | 100 | 55 |
| | | | | 4.0 | 0 | 5 | 45 | 0 | 100 | 100 | 55 |
| | | | | 1.0 | 0 | 0 | 0 | 0 | 60 | 100 | 10 |
| | | | 10 | 2.0 | 0 | 0 | 0 | 0 | 70 | 100 | 32 |
| | | | | 4.0 | 0 | 5 | 15 | 0 | 100 | 100 | 32 |
| | | | | 1.0 | 0 | 0 | 0 | 0 | 60 | 100 | 10 |
| | | | 13 | 2.0 | 0 | 0 | 10 | 20 | 80 | 100 | 40 |
| | | | | 4.0 | 0 | 0 | 12 | 20 | 80 | 100 | 70 |
| | | | | 1.0 | 0 | 10 | 0 | 0 | 0 | 90 | — |
| | | | 27 | 2.0 | 0 | 10 | 0 | 0 | 10 | 95 | — |
| | | | | 4.0 | 0 | 10 | 10 | 10 | 90 | 100 | — |
| | | | | 1.0 | 0 | 0 | 0 | 0 | 90 | 0 | — |
| | | | 7 | 2.0 | 0 | 0 | 0 | 0 | 90 | 0 | — |
| | | | | 4.0 | 0 | 0 | 0 | 20 | — | 90 | — |
| | | | | 1.0 | 0 | 0 | 0 | 0 | 60 | 95 | — |
| | | | 20 | 2.0 | 0 | 0 | 0 | 0 | 100 | — | — |
| | | | | 4.0 | 0 | 0 | 20 | 10 | 100 | 95 | — |
| | | | | 1.0 | 0 | 0 | 0 | 0 | 90 | 90 | — |
| | | | 21 | 2.0 | 0 | 0 | 10 | 0 | 100 | 95 | — |
| | | | | 4.0 | 0 | 10 | 20 | 0 | 100 | 100 | — |

| Substituents in the substances examined | | | | | Test plants and % damage | | | | | | | |
|---|---|---|---|---|---|---|---|---|---|---|---|---|
| R$^1$ | R$^2$ | R$^3$ | Compound no. | Appl. rate kg/ha | Echin. c.g. | Eleus. ind. | Euph. genio. | Poa- annua | Se- taria spp. | Sol- anum nigrum | Sorgh. halep. | Stel- aria media |
| CH(CH$_3$)$_2$ | CH(CH$_3$)$_2$ | | prior art | | | | | | | | | |
| (FR-PS 23 205 514) | | | | | | | | | | | | |
| | | | | 1.0 | 90 | 100 | 100 | 100 | 90 | 90 | 82 | 20 |
| | | | 4 | 2.0 | 95 | 100 | 100 | 100 | 100 | 90 | 95 | 30 |
| | | | | 4.0 | 95 | 100 | 100 | 100 | 100 | 100 | 97 | 60 |
| | | | | 1.0 | 95 | 100 | 60 | 100 | 100 | 100 | 72 | 0 |
| | | | 2 | 2.0 | 95 | 100 | 95 | 100 | 100 | 100 | 95 | 30 |
| | | | | 4.0 | 95 | 100 | 95 | 100 | 100 | 100 | 95 | 70 |
| | | | | 1.0 | 57 | 85 | 60 | 70 | 0 | 70 | 45 | 10 |
| | | | 9 | 2.0 | 92 | 100 | 60 | 100 | 15 | 70 | 75 | 80 |

Table 3-continued
Removal of unwanted plants by, and tolerance of crop plants to, thiol carbamates in the greenhouse; preemergence treatment Basic molecule:
$$\begin{array}{c}R^1\\ \diagdown\\ N-C-S-R^3\\ \diagup \; \| \\ R^2 \; O\end{array}$$

| Compound no. | Appl. rate kg/ha | | | | | | | |
|---|---|---|---|---|---|---|---|---|
| | 4.0 | 95 | 100 | 90 | 100 | 40 | 100 | 90 | 80 |
| | 1.0 | 55 | 22 | 50 | 0 | 30 | 90 | 15 | 70 |
| 10 | 2.0 | 80 | 85 | 50 | 0 | 45 | 90 | 20 | 80 |
| | 4.0 | 80 | 95 | 95 | 0 | 65 | 100 | 50 | 80 |
| | 1.0 | 20 | 52 | 20 | 80 | 0 | 90 | 15 | 0 |
| 13 | 2.0 | 85 | 95 | 20 | 90 | 0 | 90 | 45 | 0 |
| | 4.0 | 95 | 100 | 70 | 90 | 55 | 100 | 67 | 0 |
| | 1.0 | 60 | 50 | — | 90 | 10 | 25 | 10 | 0 |
| 27 | 2.0 | 95 | 90 | — | 100 | 80 | 60 | 60 | 0 |
| | 4.0 | 95 | 90 | — | 100 | 85 | 90 | 70 | 0 |
| | 1.0 | — | — | 90 | 40 | 0 | 90 | — | 0 |
| 7 | 2.0 | — | — | 90 | 90 | — | 90 | — | 0 |
| | 4.0 | — | — | 90 | 100 | — | 100 | — | 0 |
| | 1.0 | 60 | 80 | 30 | 90 | 20 | 30 | 10 | 0 |
| 20 | 2.0 | 90 | 95 | 30 | 100 | 75 | 30 | 65 | 0 |
| | 4.0 | 95 | 95 | 70 | 100 | 95 | 70 | 95 | 0 |
| | 1.0 | 85 | 90 | 100 | 100 | 55 | 70 | 60 | 0 |
| 21 | 2.0 | 95 | 95 | 100 | 100 | 85 | 80 | 60 | 0 |
| | 4.0 | 95 | 95 | 70 | 100 | 95 | 70 | 95 | 0 |

| Substituents in the substances examined | | | Compound no. | Appl. rate kg/ha | Test plants % damage | | | | | | |
|---|---|---|---|---|---|---|---|---|---|---|---|
| $R^1$ | $R^2$ | $R^3$ | | | Brassica napus | Glycine max | Gossyp. hirs. | Zea mays | Alopec. myosur | Amar. retro. | Cyperus escul. |
| | | | 14 | 1.0 | 0 | 0 | 5 | 0 | 100 | 90 | 20 |
| | | | | 2.0 | 0 | 0 | 12 | 10 | 100 | 90 | 50 |
| | | | | 4.0 | 0 | 0 | 12 | 10 | 100 | 100 | 77 |
| | | | 17 | 1.0 | 0 | 0 | 10 | 0 | 60 | 100 | 15 |
| | | | | 2.0 | 0 | 0 | 17 | 0 | 100 | 100 | 30 |
| | | | | 4.0 | 0 | 5 | 32 | 0 | 100 | 100 | 42 |
| | | | 5 | 1.0 | 0 | 0 | 0 | 0 | 90 | 90 | 35 |
| | | | | 2.0 | 0 | 0 | 2 | 0 | 90 | 90 | 40 |
| | | | | 4.0 | 0 | 5 | 5 | 40 | 100 | 100 | 50 |
| cycloheptyl | | $C_2H_5$ | prior art | 1.0 | 0 | — | 60 | — | 100 | — | 10 |
| | | | | 2.0 | 0 | — | 92 | — | 100 | — | 40 |
| | | | | 4.0 | 0 | — | 92 | — | 100 | — | 65 |
| $C_4H_9$n | $C_2H_5$ | $C_2H_7$n | " | 1.0 | — | 5 | 0 | 0 | — | 30 | — |
| | | | | 2.0 | — | 5 | 10 | 0 | — | 70 | — |
| | | | | 4.0 | — | 25 | 20 | 10 | — | 95 | — |
| $C_3H_7$i | $C_3H_7$i | $CH_2-CCl_2-CH$ (Cl Cl on central C) | " | 1.0 | 0 | 0 | 5 | 0 | 100 | 40 | 0 |
| | | | | 2.0 | 0 | 15 | 17 | 0 | 100 | 40 | 10 |
| | | | | 4.0 | 0 | 35 | 22 | 15 | 100 | 90 | 40 |
| $C_3H_7$i | $C_3H_7$i | $C_2H_5$ | " | 1.0 | 0 | 5 | 5 | 0 | 70 | 20 | 55 |
| | | | | 2.0 | 0 | 5 | 10 | 0 | 90 | 20 | 75 |
| | | | | 4.0 | 0 | 25 | 15 | 20 | 100 | 100 | 75 |
| $C_2H_5$ | $C_2H_5$ | $CH_2$-C$_6H_4$-Cl | " | 1.0 | 0 | 0 | 0 | 10 | 100 | 95 | 30 |
| | | | | 2.0 | 0 | 0 | 7 | 20 | 100 | 95 | 40 |
| | | | | 4.0 | 0 | 10 | 7 | 20 | 100 | 100 | 40 |

| Substituents in the substances examined | | | Compound no. | Appl. rate kg/ha | Test plants and % damage | | | | | | | |
|---|---|---|---|---|---|---|---|---|---|---|---|---|
| $R^1$ | $R^2$ | $R^3$ | | | Echin. c.g. | Eleus. ind. | Euph. genic. | Poa- anua | Setaria spp. | Solanum nigrum | Sorgh. halep. | Stelaria media |
| | | | 14 | 1.0 | 80 | 85 | 30 | 90 | 40 | 90 | 45 | 0 |
| | | | | 2.0 | 95 | 97 | 70 | 100 | 95 | 90 | 85 | 0 |
| | | | | 4.0 | 97 | 100 | 100 | 100 | 100 | 80 | 90 | 0 |
| | | | 17 | 1.0 | 85 | 85 | 90 | 100 | 35 | 100 | 47 | 100 |
| | | | | 2.0 | 95 | 100 | 100 | 100 | 65 | 100 | 92 | 100 |
| | | | | 4.0 | 97 | 100 | 100 | 100 | 100 | 100 | 92 | 100 |
| | | | 5 | 1.0 | 55 | 60 | 45 | 80 | 5 | 30 | 15 | 0 |
| | | | | 2.0 | 92 | 97 | 45 | 90 | 20 | 30 | 40 | 0 |
| | | | | 4.0 | 95 | 100 | 80 | 100 | 60 | 90 | 55 | 60 |
| cycloheptyl | | $C_2H_5$ | prior art | 1.0 | 67 | 82 | — | 0 | 65 | — | 10 | 0 |
| | | | | 2.0 | 80 | 92 | — | 30 | 100 | — | 50 | 20 |
| | | | | 4.0 | 92 | 92 | — | 90 | 100 | — | 70 | 20 |
| $C_4H_9$n | $C_2H_5$ | $C_2H_7$n | " | 1.0 | 20 | 60 | 20 | — | 20 | 0 | 340 | — |
| | | | | 2.0 | 60 | 90 | 20 | — | 60 | 0 | 70 | — |
| | | | | 4.0 | 70 | 90 | 90 | — | 80 | 30 | 90 | — |
| $C_3H_7$i | $C_3H_7$i | $CH_2-CCl_2-CH$ | " | 1.0 | 15 | 92 | 80 | 100 | 90 | 50 | 67 | 0 |
| | | | | 2.0 | 75 | 95 | 80 | 100 | 95 | 80 | 85 | 0 |
| | | | | 4.0 | 87 | 100 | 80 | 100 | 100 | 80 | 90 | 0 |
| $C_3H_7$n | $C_3H_7$n | $C_2H_5$ | " | 1.0 | 50 | 72 | 30 | 90 | 65 | 0 | 40 | 40 |
| | | | | 2.0 | 50 | 95 | 30 | 90 | 95 | 0 | 57 | 40 |
| | | | | 4.0 | 60 | 95 | 100 | 100 | 100 | 30 | 70 | 50 |

Table 3-continued
Removal of unwanted plants by, and tolerance of crop plants to, thiol carbamates in the greenhouse; preemergence treatment Basic molecule: $\underset{R^2}{\overset{R^1}{\diagdown}}N-\underset{\underset{O}{\parallel}}{C}-S-R^3$

| | | | | | | | | | | | |
|---|---|---|---|---|---|---|---|---|---|---|---|
| C$_2$H$_5$ | C$_2$H$_5$ | CH$_2$—⌬—Cl | " | 1.0 | 80 | 100 | 90 | 100 | 80 | 50 | 90 | 0 |
| | | | | 2.0 | 95 | 100 | 90 | 100 | 100 | 70 | 90 | 0 |
| | | | | 4.0 | 95 | 100 | 100 | 100 | 100 | 90 | 95 | 0 |

0 = no damage
100 = complete destruction

Table 4
Hebicidal action of new isoxazolylalkylthiol carbamates in the greenhouse; pre- and postemergence application

| Compound no. | Appl. rate kg/ha | Method | Cyperus escul. | Echino-chloa crus galli | Lolium multifl. |
|---|---|---|---|---|---|
| 26 | 3.0 | PRE | — | 90 | 90 |
| | 3.0 | POST | 90 | 90 | 90 |
| 28 | 3.0 | PRE | — | 90 | 70 |
| | 3.0 | POST | 90 | 90 | 90 |
| 29 | 3.0 | PRE | — | 90 | 90 |
| | 3.0 | POST | 70 | 90 | 50 |
| 33 | 3.0 | PRE | — | 0 | 0 |
| | 3.0 | POST | 0 | 90 | 50 |
| 38 | 3.0 | PRE | — | 90 | 30 |
| | 3.0 | POST | 90 | 90 | 90 |

PRE = preemergence treatment
POST = postemergence treatment
0 = no damage
100 = complete destruction

Table 5
Selective control of grassy weeds in beet with various thiol carbamates in the open; preplant incorporation Basic molecule: $\underset{R^2}{\overset{R^1}{\diagdown}}N-\underset{\underset{O}{\parallel}}{C}-S-R^3$

| Substituents in the compounds examined | | | Compound No. | Appl. rate kg/ha | Beta vulgaris | Alopecurus myosuroides |
|---|---|---|---|---|---|---|
| R$^1$ | R$^2$ | R$^3$ | | | | |
| | | | 2 | 2.0 | 5 | 95 |
| | | | 16 | 2.0 | 0 | 75 |
| | | | 3 | 2.0 | 5 | 80 |
| | | | 10 | 4.0 | 0 | 65 |
| | | | 13 | 4.0 | 0 | 50 |
| | | | 9 | 4.0 | 50 | 70 |
| | | | 14 | 4.0 | 50 | 90 |
| C$_3$H$_7$i | C$_3$H$_7$i | CH$_2$—C=C—Cl (Cl Cl) | prior art | 2.0 | 0 | 30 |
| | | | | 4.0 | 0 | 80 |
| C$_3$H$_7$n | C$_3$H$_7$n | C$_2$H$_5$ | prior art | 2.0 | 10 | 80 |
| | | | | 4.0 | 30 | 95 |

0 = no damage
100 = complete destruction

Table 6
Herbicidal action and crop plant tolerance in the greenhouse; preemergence application Basic molecule: $\underset{R^2}{\overset{R^1}{\diagdown}}N-\underset{\underset{O}{\parallel}}{C}-S-R^3$

| Substituents in the compounds examined | | | Compound no. | Appl. rate kg/ha | Beta vulg. | Brassica Napus | Gossyp. hirs. | Tritic. aestivum | Amar. retr. | Cynod. dactyl. | Echin. c.g. | Setaria spp. | Solanum nigrum | Sorghum halepense |
|---|---|---|---|---|---|---|---|---|---|---|---|---|---|---|
| R$^1$ | R$^2$ | R$^3$ | | | | | | | | | | | | |
| | | | 1 | 2.0 | 0 | 0 | 5 | 0 | 90 | 75 | 87 | 50 | 95 | 70 |
| | | | | 4.0 | 0 | 0 | 10 | 0 | 100 | 95 | 92 | 65 | 95 | 75 |
| C$_2$H$_5$ | 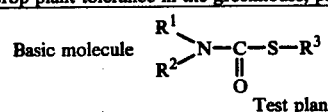 | C$_2$H$_5$ | prior art | 2.0 | 0 | 30 | 20 | 100 | 85 | 97 | 92 | 95 | 30 | 90 |
| | | | | 4.0 | 10 | 40 | 40 | 100 | 92 | 97 | 92 | 95 | 90 | 95 |
| | | | 31 | 2.0 | 0 | 0 | 0 | 0 | 95 | — | 95 | 85 | 80 | 60 |
| | | | | 4.0 | 0 | 0 | 10 | 10 | 100 | — | 95 | 90 | 90 | 60 |

0 = no damage
100 = complete destruction

Table 7

Tolerance of some thiol carbamates by rape and spring wheat in the open; preplant incorporation Basic molecule: $\begin{array}{c} R^1 \\ R^2 \end{array}\!\!N\!-\!\overset{\overset{\displaystyle O}{\|}}{C}\!-\!S\!-\!R^3$

| Substituents in the compounds examined | | | Compound no. | Appl. rate kg/ha | Test plants and % damage | | |
|---|---|---|---|---|---|---|---|
| $R^1$ | $R^2$ | $R^3$ | | | Brassica napus | Triticum aestivum[+] | Alopecurus myosuroides[++] |
| | | | 4 | 2.0 | 0 | 0 | 82 |
| | | | | 4.0 | 0 | 5 | 95 |
| $C_3H_7i$ | $C_3H_7i$ | $CH_2\!-\!\underset{Cl}{C}\!=\!CH$ | prior art | 2.0 | 0 | — | 86 |
| | | | | 4.0 | 0 | — | 100 |
| $C_3H_7i$ | $C_3H_7i$ | $CH_2\!-\!\underset{Cl}{C}\!=\!\underset{Cl}{C}\!-\!Cl$ | prior art | 2.0 | 0 | 2 | 58 |
| | | | | 4.0 | 0 | 8 | 98 |
| $C_4H_9i$ | $C_4H_9i$ | $C_2H_5$ | prior art | 1.5 | 0 | 15 | 30 |
| | | | | 3.0 | 0 | 82 | 75 |
| $C_3H_7n$ | $C_3H_7n$ | $C_2H_5$ | prior art | 1.5 | 0 | 12 | 25 |
| | | | | 3.0 | 10 | 88 | 82 |

0 = no damage
100 = complete destruction
[+] = spring wheat
[++] = grassy weed as an indicator of the herbicidal action

Table 8

Action of some thiol carbamates when applied by different methods in cereals in the open Basic molecule: $\begin{array}{c} R^1 \\ R^2 \end{array}\!\!N\!-\!\overset{\overset{\displaystyle O}{\|}}{C}\!-\!S\!-\!R^3$

| Substituents in the compounds examined | | | Compound no. | Appl. rate kg/ha | Appl. method 1) | Test plants and % damage | | | |
|---|---|---|---|---|---|---|---|---|---|
| $R^1$ | $R^2$ | $R^3$ | | | | Hordeum vulgare 2) | Tritic. aest. 3) | Alopec. myosur. | Matric. spp. |
| | | | 4 | 2.0 | I | 2.5 | 0 | 68 | 9 |
| | | | | 2.0 | II | 0 | 1.2 | 85 | 54 |
| | | | | 2.0 | III | 0 | 0 | 93 | 65 |
| | | | | 2.0 | IV | 0 | — | 72 | 20 |
| $C_3H_7i$ | $C_3H_7i$ | $CH_2\!-\!\underset{Cl}{C}\!=\!\underset{Cl}{C}$ | prior art | 2.0 | I | 0 | 2.5 | 70 | 6 |
| | | | | 2.0 | II | 0 | 0 | 51 | 23 |
| | | | | 2.0 | III | 0 | 0 | 42 | 20 |
| | | | | 2.0 | IV | — | — | 65 | 5 |
| $C_2H_5$ | $C_2H_5$ | $CH_2\!-\!\text{C}_6H_4\!-\!Cl$ | prior art | 2.0 | I | 2.5 | 0 | 57 | 0 |
| | | | | 2.0 | II | 0 | 0 | 64 | 30 |
| | | | | 2.0 | III | 0 | 5 | 65 | 65 |
| | | | | 2.0 | IV | 8 | — | 59 | 6 |

1) I = Preplant incorporation
II = Preemergence
III = Application to emerging plants
IV = Postemergence
2) winter barley
3) winter wheat
0 = no damage
100 = complete destruction

Table 9

Action of 3-methyl-5-isoxazolylmethyl-N,N-diisopropylthiol carbamate applied preemergence in the open without incorporation; comparison with prior art compounds

| Compound | Appl. rate | Test plants and % damage | | |
|---|---|---|---|---|
| | | Zea mays | Echinochloa crus galli | Chenopodium album |
| $C_3H_7i$–N($C_3H_7i$)–C(=O)–S–CH$_2$–(3-methylisoxazol-5-yl) (Active ingredient no. 4) | 2.0 | 0 | 80 | 25 |
| | 4.0 | 0 | 95 | 60 |

Table 9-continued

Action of 3-methyl-5-isoxazolylmethyl-N,N-diisopropylthiol carbamate applied preemergence in the open without incorporation; comparison with prior art compounds

| Compound | Appl. rate | Test plants and % damage | | |
|---|---|---|---|---|
| | | Zea mays | Echinochloa crus galli | Chenopodium album |
| $C_3H_7i$ $\diagdown$ N—C(=O)—S—$CH_2$—C(Cl)=CH(Cl) / $C_3H_7i$ | 2.0 | — | 49 | 15 |
| | 4.0 | — | 85 | 35 |
| prior art | | | | |
| $C_2H_5$-phenyl ($C_2H_5$)-N($CH_2$—O—$CH_3$)—C(=O)—$CH_2$—Cl | 2.0 | 0 | 65 | 20 |
| | 4.0 | 0 | 95 | 70 |
| prior art | | | | |
| $CH_3$—CH—$CH_3$ phenyl—N—C(=O)—$CH_2$—Cl | 2.0 | 0 | 55 | 62 |
| | 4.0 | 0 | 70 | 75 |
| prior art | | | | |

0 = no damage
100 = complete destruction

Table 10

Herbicidal action and crop plant tolerance of some thiol carbamates in the greenhouse; postemergence treatment Basic molecule: $R^1R^2N-C(=O)-S-R^3$

| $R^1$ | $R^2$ | $R^3$ | Compound no. | Appl.rate kg/ha | Beta vulg. | Gossyp. hirs. | Alop. myo. | Avena fat. | Cypre. escul. | Echin. c.g. | Eleus. indic. | Set. fab. |
|---|---|---|---|---|---|---|---|---|---|---|---|---|
| | | | 4. | 1.0 | 0 | 0 | 80 | 75 | 65 | 78 | 20 | 55 |
| | | | | 2.0 | 0 | 0 | 90 | 88 | 65 | 78 | 60 | 70 |
| $C_3H_7i$ | $C_3H_7i$ | $CH_2$—C(Cl)=CH(Cl) | prior art | 1.0 | 0 | — | 50 | 70 | — | — | — | — |
| | | | | 2.0 | 0 | — | 90 | 70 | — | — | — | — |
| $C_2H_5$ | $C_2H_5$ | $CH_2$—(p-Cl-phenyl) | prior art | 1.0 | — | 0 | — | 20 | 10 | 45 | 10 | 55 |
| | | | | 2.0 | — | 5 | — | 60 | 30 | 48 | 50 | 55 |

0 = no damage
100 = complete destruction

Table 11

Phytotoxicity of the vapor phase of some thiol carbamates to the crop plant oats Basic molecule: $R^1R^2N-C(=O)-S-R^3$

| $R^1$ | $R^2$ | $R^3$ | Compound no. | Appl.rate kg/ha | Green weight of Avena sativa in g | | | |
|---|---|---|---|---|---|---|---|---|
| | | | | | directly treated | | in parpllel Vessel | |
| $C_3H_7i$ | $C_3H_7i$ | $CH_2$—C(Cl)=CH(Cl) | | 1.0 | 1.3 | CDE | 2.7 | FG |
| | | | | 2.0 | 0.6 | ABC | 1.9 | EF |
| | | | | 4.0 | 0.2 | AB | 1.1 | BCDE |
| $C_3H_7i$ | $C_3H_7i$ | $CH_2$—C(Cl)=C(Cl)(Cl) | | 1.0 | 1.8 | DEF | 2.7 | FG |
| | | | | 2.0 | 1.0 | BCDE | 1.5 | CDE |
| | | | | 4.0 | 0.82 | ABCD | 1.7 | DEF |
| | | | 4 | 1.0 | 1.5 | CDE | 3.7 | H |
| | | | | 2.0 | 0.8 | ABCD | 3.6 | GH |
| | | | | 4.0 | 0.2 | AB | 3.5 | GH |

Table 11-continued
Phytotoxicity of the vapor phase of some thiol carbamates to the crop plant oats Basic molecule:
$$R^1\text{—}N(R^2)\text{—}C(=O)\text{—}S\text{—}R^3$$

| $R^1$ | $R^2$ | $R^3$ | Compound no. | Appl.rate kg/ha | Green weight of Avena sativa in g directly treated | in parpllel Vessel |
|---|---|---|---|---|---|---|
| Control (untreated) | | | | — | | 3.7 H |

Values having a letter in common are not significantly different (Duncan's new multiple raange test, level 0.05)
22.Steel, R.G.D. and Torrie, J.H. - Principles and Procedures of Satistics, New York, Toronto, London 1960, pp, 481

Table 12
Selective herbicidal action in rice; preemergence application in the greenhouse

| Compound no. | kg/ha | Oryza sativa | Echinochloa crus galli | Cynodon dactylon | Setaria spp. |
|---|---|---|---|---|---|
| 34 | 0.5 | 13 | 79 | 75 | 72 |
|  | 1.0 | 19 | 86 | 95 | 92 |

0 = no damage
100 = nonemergence or complete withering

In view of the methods of application possible with the compounds of the invention, they, or compositions containing them, may be used not only in the crops listed in the tables but also in a wide variety of other crops for combatting unwanted plant growth. Application rates may be from 0.1 to 15 kg/ha and more, depending on the object to be combatted. Individual crop plants are listed below:

| Botanical name | English name |
|---|---|
| Allium cepa | onions |
| Ananas comosus | pineapple |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Citrus limon | lemons |
| Citrus maxima | grapefruit |
| Citrus reticulata | |
| Citrus sinensis | orange trees |
| Coffea arabica (Coffea canaphora, Coffea liberica) | coffee plants |
| Cucumis melo | melons |
| Cucumis sativus | cucumber |
| Cynodon dactylon | Bermudagrass in turf and lawns |
| Daucus carota | carrots |
| Elaeis guineensis | oil palms |
| Fragaria vesca | strawberries |
| Glycine max | soybeans |
| Gossypium hirsutum (Gossypium arboreum Gossypium herbeceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Lactuca sativa | lettuce |
| Lens culinaris | lentils |
| Linum usitatissimum | flax |
| Lycopersicon lycopersicum | tomatoes |
| Malus spp. | apple tree |
| Manihot esculenta | cassava |
| Medicago sativa | alfalfa (lucerne) |
| Mentha piperita | peppermint |
| Musa spp. | banana plants |
| Nicotiana tabacum | tobacco |

-continued

| Botanical name | English name |
|---|---|
| (N. rustica) | |
| Olea europaea | olive trees |
| Panicum miliaceum | |
| Phaseolus lunatus | limabeans |
| Phaseolus mungo | mungbeans |
| Phaseolus vulgaris | snapbeans, green beans, dry beans |
| Pennisetum glacum | |
| Petroselinum crispum spp. tuberosum | parsley |
| Picea abies | Norway spruce |
| Abies alba | fir |
| Pinus spp. | pine trees |
| Pisum sativum | English peas |
| Prunus avium | cherry trees |
| Prunus domestica | plum trees |
| Prunus persica | peach trees |
| Pyrus communis | pear trees |
| Ribes sylvestre | redcurrants |
| Ribes uva-crispa | |
| Ricinus communis | |
| Saccharum officinarum | sugar cane |
| Secale cereale | rye |
| Sesamum indicum | Sesami |
| Solanum tuberosum | Irish potatoes |
| Sorghum bicolor (s. vulgare) | grain sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

The new isoxazolylalkylthiol carbamates of the invention may be mixed with numerous respresentatives of other groups of herbicidal active ingredients. Such combinations broaden the spectrum of action and have in some cases synergistic effects. The following compounds are examples of those which can be mixed with the compounds of the invention:

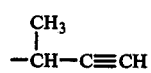

| R | $R^1$ |
|---|---|
| 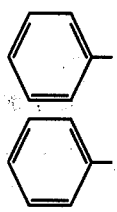 | isopropyl |
| | $-CH(CH_3)-C\equiv CH$ |

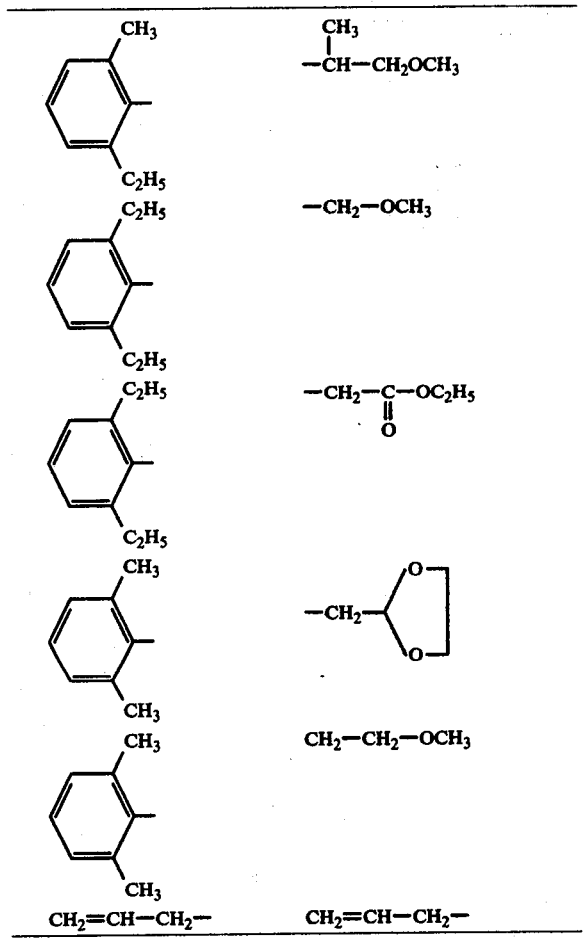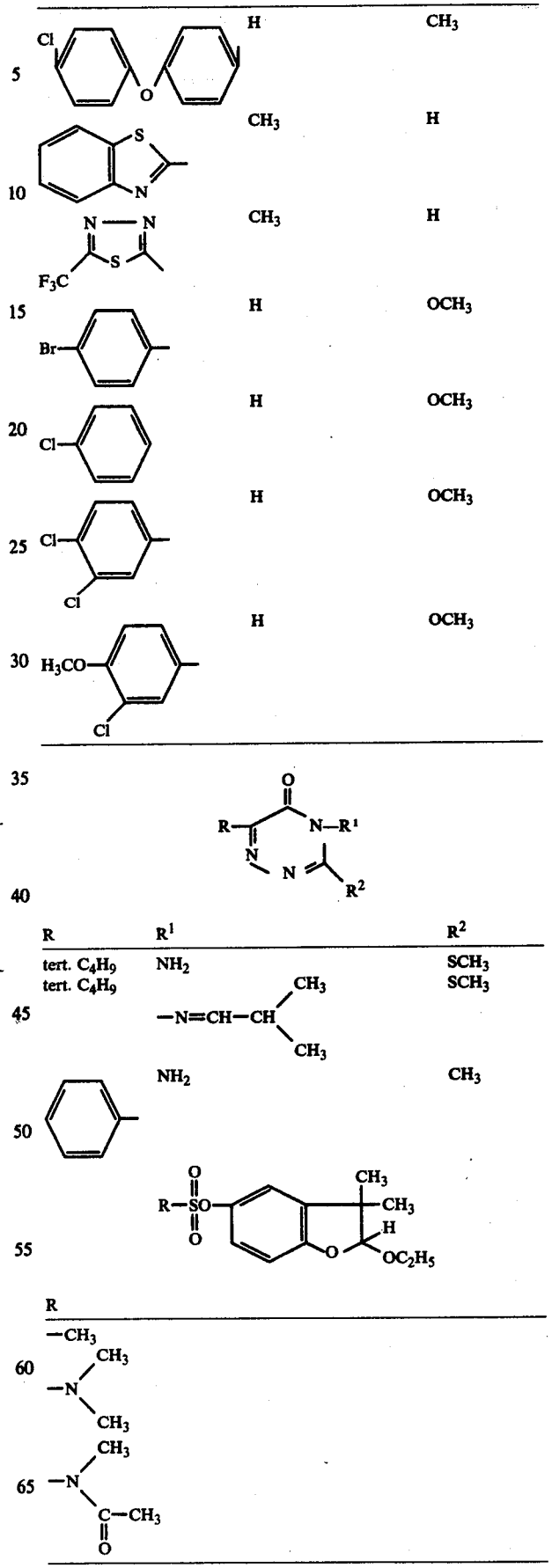

-continued

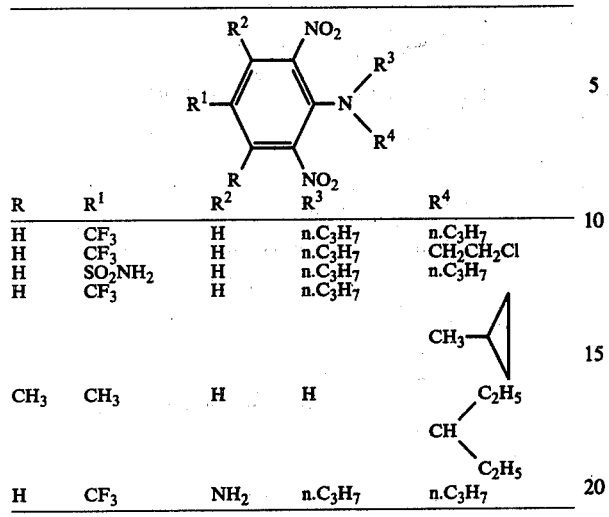

| R | R¹ | R² | R³ | R⁴ |
|---|----|----|----|----|
| H | CF₃ | H | n.C₃H₇ | n.C₃H₇ |
| H | CF₃ | H | n.C₃H₇ | CH₂CH₂Cl |
| H | SO₂NH₂ | H | n.C₃H₇ | n.C₃H₇ |
| H | CF₃ | H | n.C₃H₇ | CH(CH₃)CH(C₂H₅)₂ |
| CH₃ | CH₃ | H | H | CH(C₂H₅)CH(C₂H₅)₂ |
| H | CF₃ | NH₂ | n.C₃H₇ | n.C₃H₇ |

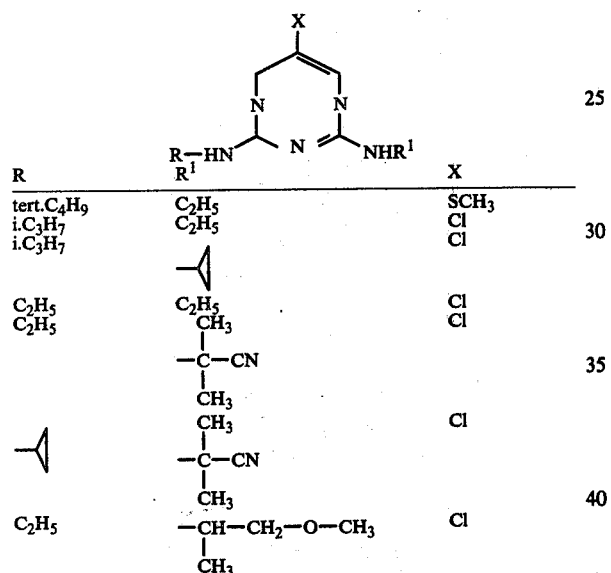

| R | R¹ | X |
|---|----|---|
| tert.C₄H₉ | C₂H₅ | SCH₃ |
| i.C₃H₇ | C₂H₅ | Cl |
| i.C₃H₇ | cyclopropyl | Cl |
| C₂H₅ | C₂H₅ | Cl |
| C₂H₅ | —C(CH₃)₂—CN | Cl |
| cyclopropyl | —C(CH₃)₂—CN | Cl |
| C₂H₅ | —CH(CH₃)—CH₂—O—CH₃ | Cl |

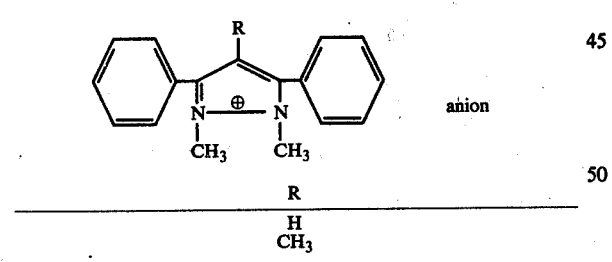

anion

| R |
|---|
| H |
| CH₃ |

CH₃—CCl₂—C(=O)—ONa

CCl₃—C(=O)—ONa

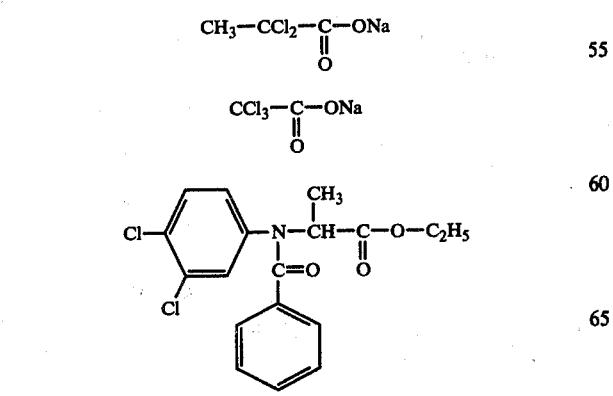

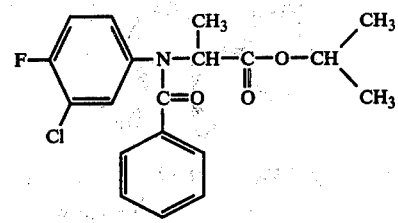

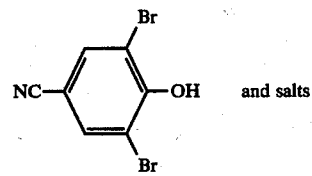 and salts

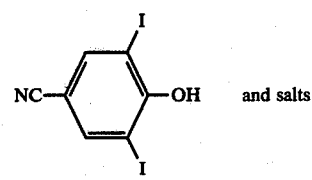 and salts

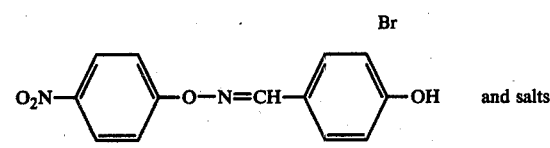 and salts

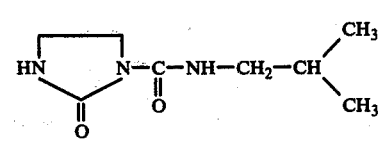

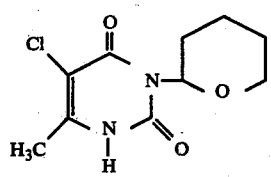

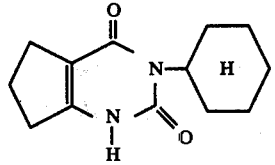

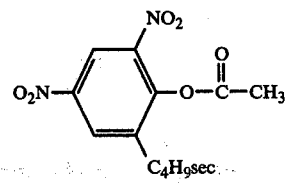

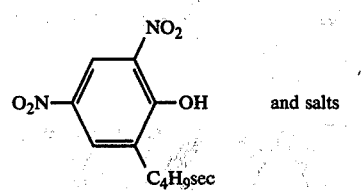 and salts

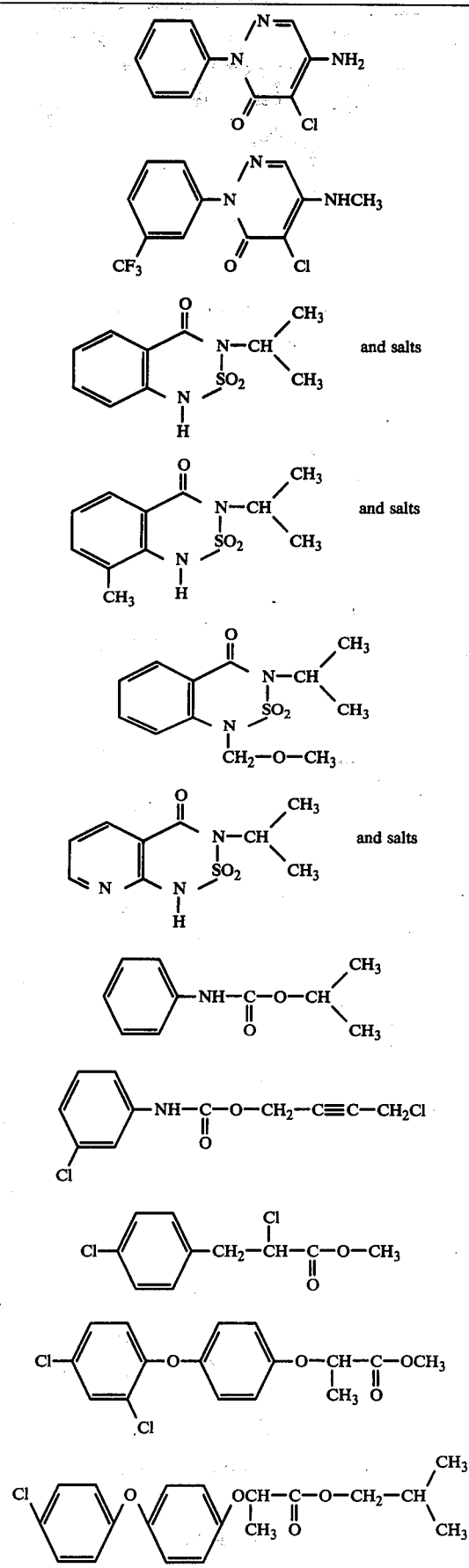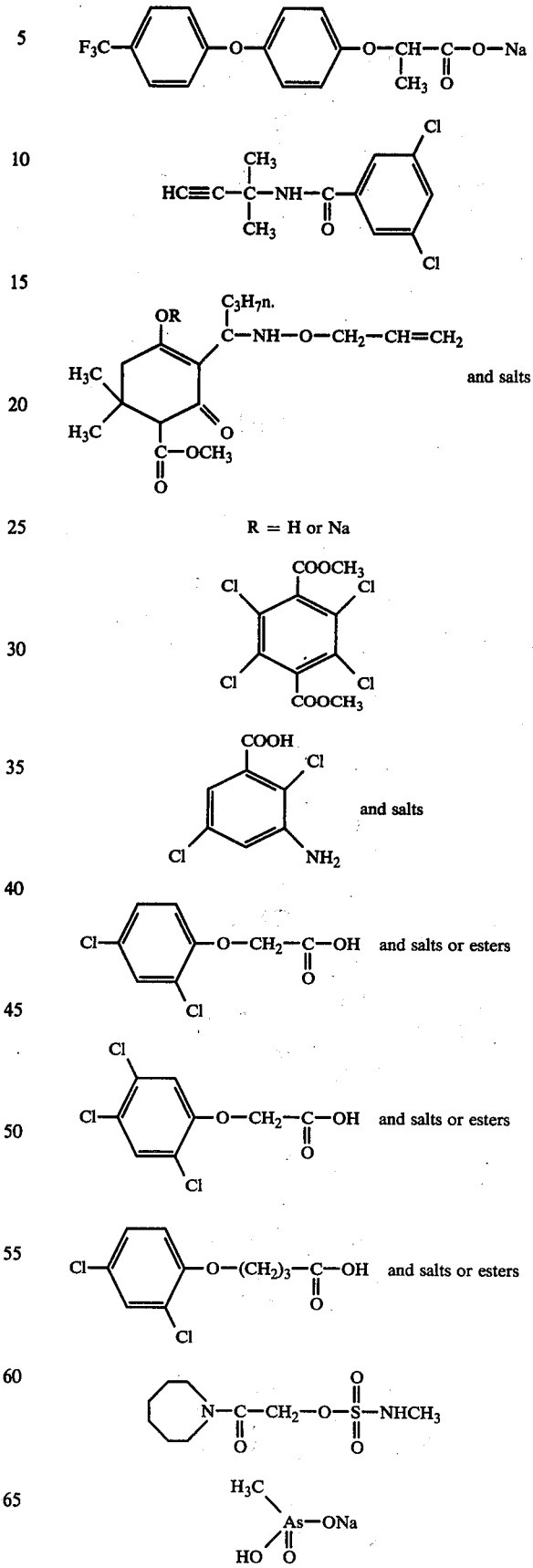

-continued

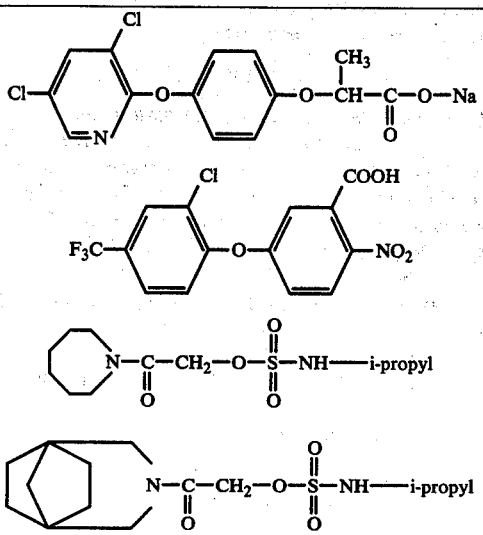

It is also useful to be able to apply the new compounds according to the invention, either alone or in combination with other herbicides, in admixture with other crop protection agents, e.g., agents for combatting pests and phytopathogenic fungi, and growth regulators. The new compounds may also be mixed with mineral fertilizer solutions used to overcome nutritional or trace element deficiencies.

Application may be effected for instance in the form of directly sprayable solutions, powders, suspensions (including high-percentage aqueous, oily or other suspensions), dispersions, emulsions, oil dispersion, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions or individual active ingredients (if desired, immediately before use (tank-mix)) oils of various types, wetting agents or adherents, herbicides, fungicides, nematocides, insecticides, bactericides, trace elements, fertilizers, antifoams (e.g., silicones), growth regulators, antidotes and other herbicidally effective compounds. The last-mentioned herbicidal compounds may also be applied before or after the individual active ingredients according to the invention or compositions thereof.

These agents may be added to the herbicides according to the invention in a ratio by weight of from 1:10 to 10:1. The same applies to oils, wetting agents and adherents, fungicides, nematocides, insecticides, bactericides, antidotes and growth regulators.

EXAMPLE 4

90 parts by weight of compound 1 is mixed with 10 parts by weight of N-methyl-α-pyrrolidone. A mixture is obtained which is suitable for application in the form of very fine drops.

EXAMPLE 5

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 6

20 parts by weight of compound 3 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound 4 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 9

3 parts by weight of compound 4 is intimately mixed with 97 parts by weight of particulate kaolin. A dust is obtained containing 3% by weight of the active ingredient.

EXAMPLE 10

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 11

40 parts by weight of compound 5 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 12

20 parts of compound 6 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. An isoxazolylmethylthiol carbamate of the formula

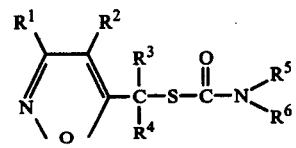

wherein $R^1$ denotes hydrogen, lower alkyl of 1 to 6 carbon atoms, unsubstituted or lower alkyl-substituted cycloalkyl of 3 to 8 ring carbon atoms, benzyl, phenylethyl, phenyl chlorophenyl, fluorophenyl, dichlorophenyl or trifluoromethylphenyl, $R^2$ denotes hydrogen, lower alkyl of 1 to 6 carbon atoms, lower alkyl of 1 to 6 carbon atoms substituted by chlorine, phenyl or halogen, $R^3$ denotes hydrogen or lower alkyl, $R^4$ denotes hydrogen or lower alkyl, and $R^5$ and $R^6$ are identical or different and each denotes lower alkyl of 1 to 6 carbon atoms, lower alkenyl of 2 to 4 carbon atoms, unsubstituted or lower alkyl-substituted cycloalkyl of 3 to 8 ring carbon atoms, alkoxyalkyl of 2 to 6 carbon atoms or haloalkyl of 1 to 4 carbon atoms, and additionally $R^5$ and $R^6$ together with the nitrogen atom denote an unsubstituted or lower alkyl-substituted heterocyclic ring selected from the group consisting of azetidine, 2-methylazetidine, 2,4-dimethylazetidine, 2,4,4-trimethylazetidine, pyrrolidine, 2-methylpyrrolidine, 2-ethylpyrrolidine, 2,5-dimethylpyrrolidine, piperidine, 2-methylpiperidine, 2-ethylpiperidine, 2-methyl-5-ethylpiperidine, hexahydroazepine, 2-methylhexahydroazepine, 2,3-dimethylhexahydroazepine, heptamethyleneimine, bicyclo-[3,2,2]-3-and 3,5-dimethylmorpholine.

2. 3-methyl-5-isoxazolylmethyl-N-ethyl-N-cyclohexylthiol carbamate.

3. 3-ethyl-5-isoxazolylmethyl-N,N-diisopropylthiol carbamate.

4. 3-methyl-5-isoxazolylmethyl-N,N-diethylthiol carbamate.

* * * * *

UNITED STATES PATENT AND TRADEMARK OFFICE
CERTIFICATE OF CORRECTION

PATENT NO. : 4,124,591
DATED : Nov. 7, 1978
INVENTOR(S) : EICKEN ET AL

It is certified that error appears in the above-identified patent and that said Letters Patent are hereby corrected as shown below:

In the heading, after section "[22] Filed: June.27, 1977" insert the following section --[30] Foreign Application Priority Data July 28, 1976  Fed. Rep. of Germany. .2633790--.

Signed and Sealed this

First Day of May 1979

[SEAL]

Attest:

RUTH C. MASON
Attesting Officer

DONALD W. BANNER
Commissioner of Patents and Trademarks

UNITED STATES PATENT AND TRADEMARK OFFICE
CERTIFICATE OF CORRECTION

PATENT NO. : 4,124,591
DATED : November 7, 1978
INVENTOR(S) : Karl EICKEN et al.

It is certified that error appears in the above-identified patent and that said Letters Patent are hereby corrected as shown below:

Claim 1, line 46: "bicyclo-[3,2,2]-3" should read

--bicyclo-[3,2,2]-3-azanonane, morpholine, 2,6-dimethylmorpholine--.

Signed and Sealed this

Ninth Day of September 1980

[SEAL]

Attest:

SIDNEY A. DIAMOND

Attesting Officer

Commissioner of Patents and Trademarks